United States Patent
Helmrick et al.

(10) Patent No.: US 6,482,969 B1
(45) Date of Patent: Nov. 19, 2002

(54) SILICON BASED QUATERNARY AMMONIUM FUNCTIONAL COMPOSITIONS AND METHODS FOR MAKING THEM

(75) Inventors: Liza Ruth Helmrick, Plymouth, WI (US); John Joseph Kennan, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/001,760

(22) Filed: Oct. 24, 2001

(51) Int. Cl.[7] .................................................. C07F 7/10
(52) U.S. Cl. ...................... 556/420; 556/413; 556/418; 556/419; 556/423; 556/424; 556/425
(58) Field of Search ................. 556/413, 418, 556/419, 420, 423, 424, 425

(56) References Cited

U.S. PATENT DOCUMENTS

| | | | |
|---|---|---|---|
| 3,389,160 A | 6/1968 | Reid | 260/448.2 |
| 4,118,316 A | 10/1973 | Talley et al. | 210/31 C |
| 4,891,166 A | 1/1990 | Schaefer et al. | 260/404.5 |
| 4,895,964 A | 1/1990 | Margida | 556/425 |
| 5,064,544 A * | 11/1991 | Lin et al. | 556/425 X |
| 5,098,979 A | 3/1992 | O'Lenick, Jr. | 528/15 |
| 5,124,466 A * | 6/1992 | Azechi et al. | 556/425 |
| 5,164,522 A | 11/1992 | McCarthy et al. | 554/39 |
| 5,246,607 A * | 9/1993 | Schaefer et al. | 556/419 X |
| 6,242,554 B1 * | 6/2001 | Busch et al. | 556/423 X |
| 6,245,924 B1 | 6/2001 | Imperante | 556/405 |
| 6,255,511 B1 * | 7/2001 | Klein et al. | 556/425 X |

FOREIGN PATENT DOCUMENTS

| | | | |
|---|---|---|---|
| DE | 3301667 A1 | 7/1984 | |
| FR | 1589218 | 4/1970 | |
| JP | 54087709 A | 7/1979 | |
| JP | 61034004 A | 2/1986 | C08B/37/08 |
| JP | 7070204 A | 3/1995 | C08B/15/00 |
| WO | WO 99/62957 | 12/1999 | |
| WO | WO 01/41721 A1 | 6/2001 | |

OTHER PUBLICATIONS

Eugene Loubaki, Michelle Ourevitch and Sames Sicsic; "Chemical Modification of Chitosan By Glycidyl Trimethylammonium Chloride. Characterization of Modified Chitosan By 13C—And 1H–NMR Spectroscopy"; Oct. 24, 2001; European Polymers Journal; vol. 27, No. 3; 1991; pp. 311–317.

Statement as to related Applications; Oct. 24, 2001.

* cited by examiner

Primary Examiner—Paul F. Shaver
(74) Attorney, Agent, or Firm—Charles R. Richard

(57) ABSTRACT

There are disclosed novel quaternary ammonium functional silicones and silanes and methods to make quaternary ammonium functional silicones and silanes. Quaternary ammonium functionality may be provided through the use of cationizing agents.

22 Claims, No Drawings

Content abbreviated for brevity

SILICON BASED QUATERNARY AMMONIUM FUNCTIONAL COMPOSITIONS AND METHODS FOR MAKING THEM

FIELD OF THE INVENTION

This invention relates to silicon based quaternary ammonium functional compositions and to methods for making such compositions. More particularly, the invention relates to certain novel quaternary ammonium functional silicones and silanes, as well as methods to make quaternary ammonium functional silicones and silanes using cationizing agents.

BACKGROUND OF THE INVENTION

Quaternary ammonium functional organic materials are well known in the art. They can be made by methods such as the exhaustive alkylation of amines by alkyl halides. Because of their positive charge, quaternary ammonium functional organics are useful in treating materials/surfaces that are primarily negatively charged, such as in many textile and personal care applications. These materials have also been found to exhibit anti-microbial activity.

It has been found that cationic modification of polymers (including those making up fillers, fibers and surfaces, organic or silicon based) through addition or formation of quaternary ammonium functionality makes possible certain ionic interactions that are the basis of many useful properties (or their enhancement) and thus applications of such modified materials. These include increase in hydrophilic character, ability to act as a thickener and improved ability to pickup other materials such as dyes, coatings and conditioning agents.

Recently, such modification has been described for starch in PCT publication WO 99/62957 and for chitosan in the article by Loubaki et al. in 27 Eur. Polym. J. 3:311–317 (1991). In the former, the cationizing agents, 2,3-epoxypropyltrimethylammonium chloride or equivalent chlorohydrin functional materials were used. Glycidyl trimethylammonium chloride was used in the work reported in the latter reference with reaction taking place at the amino groups of the chitosan.

Quaternary ammonium functional silicones and methods for making them have been known in the art for a number of years. For example, Reid in U.S. Pat. No. 3,389,160 discloses a group of these materials and a two step method for making them. In the first step, an epoxy functional silicone is reacted with a secondary amine to form a tertiary amine functional silicone. The product is reacted with an alkyl halide to yield a quaternary ammonium functional silicone in the second step.

Margida in U.S. Pat. No. 4,895,964 discloses certain pendant quaternary ammonium functional silicones and a one step method for making them. Here, a tertiary amine salt is reacted with a pendant epoxy functional silicone. A group of terminal quaternary ammonium functional silicones is disclosed by Schaefer et al. in U.S. Pat. No. 4,891,166, as well as a method for making them, which is similar to the method in Margida, except that a terminal epoxy functional silicone is used.

McCarthy et al. in U.S. Pat. No. 5,164,522 discloses a class of quaternary ammonium functional silicones and a method for making them; the method involves treating diamine functional silicones with ethylene oxide followed by reaction with dimethyl sulfate. In U.S. Pat. No. 5,098,979 to O'Lenick, another group of quaternary ammonium functional silicones is disclosed along with a two step method for making them. This method involves reacting a silicone polyether having a terminal —OH group with epichlorohydrin (an epoxide), and the resulting product is reacted with a tertiary amine.

A group of quaternary ammonium functional silanes covalently bonded to glass is disclosed by Tally et al. in U.S. Pat. No. 4,118,316. These materials are made by reacting amino silanes and glass beads to form silanized glass, followed by treatment with a halohydrin.

Considering the large number of applications possible, such as in personal care and textiles, there is a need for new quaternary ammonium functional silicones and silanes and methods for making them. The present invention is directed to filling these needs.

SUMMARY OF THE INVENTION

It is an object of this invention to provide novel, silicon based quaternary ammonium functional compositions. Thus, the invention relates to a silicon based quaternary ammonium functional composition comprising the group:

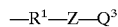

where, —$R^1$— is either a divalent hydrocarbon group, which may optionally incorporate ether or ester functionality, or —$R^{17}N(Q^1)R^{18}$—, and is covalently bonded to Si in an unsupported silicone or silane;

—Z— is —C(O)O— or —N($Q^2$)—;

—$Q^3$ is —CH($R^3$)CH(OH)YN$^+$($R^4$)($R^5$)($R^6$)X$^-$, hydrogen or a monovalent hydrocarbon group that may optionally incorporate hydroxy, diol, amide, ether or ester functionality;

—$R^{17}$— and —$R^{18}$— are independently divalent hydrocarbon groups that may optionally incorporate ether or ester functionality;

—$Q^1$ and $Q^2$ are independently —CH($R^3$)CH(OH)YN$^+$($R^4$)($R^5$)($R^6$)X$^-$, hydrogen or a monovalent hydrocarbon group that may optionally incorporate hydroxy, diol, amide, ether or ester functionality;

Y is a divalent hydrocarbon group;

$R^3$ is a monovalent hydrocarbon group or hydrogen;

$R^4$, $R^5$ and $R^6$ are independently monovalent hydrocarbon groups; and

X$^-$ is a counter ion, with the proviso that at least one of —$Q^1$, —$Q^2$ and —$Q^3$ is —CH($R^3$)CH(OH)YN$^+$($R^4$)($R^5$)($R^6$)X$^-$.

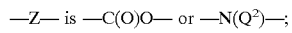

It is a further object of this invention to provide methods to make silicon based quaternary ammonium functional compositions. Thus, this invention further relates to a method of making a silicon based quaternary ammonium functional composition, the method comprising:

reacting (1) a quaternary ammonium compound having a substituent group, the substituent group having epoxide or halohydrin functionality, with (2) a silicon based material having an organofunctional group, the silicon based material being an unsupported silicone or silane and the organofunctional group having carboxy or amino functionality.

DETAILED DESCRIPTION OF THE INVENTION

The compositions according to the present invention are silicon based quaternary ammonium functional compositions, including those that comprise the group:

$-R^1-Z-Q^3$ where, $-R^1-$ is either a divalent hydrocarbon group, which may optionally incorporate ether or ester functionality, or $-R^{17}N(Q^1)R^{18}-$, and is covalently bonded to Si in an unsupported silicone or silane;

$-Z-$ is $-C(O)O-$ or $-N(Q^2)-$;

$-Q^3$ is $-CH(R^3)CH(OH)YN^+(R^4)(R^5)(R^6)X^-$, hydrogen or a monovalent hydrocarbon group that may optionally incorporate hydroxy, diol, amide, ether or ester functionality;

$-R^{17}-$ and $-R^{18}-$ are independently divalent hydrocarbon groups that may optionally incorporate ether or ester functionality;

$-Q^1$ and $Q^2$ are independently $-CH(R^3)CH(OH)YN^+(R^4)(R^5)(R^6)X^-$, hydrogen or a monovalent hydrocarbon group that may optionally incorporate hydroxy, diol, amide, ether or ester functionality;

Y is a divalent hydrocarbon group;

$R^3$ is a monovalent hydrocarbon group or hydrogen;

$R^4$, $R^5$ and $R^6$ are independently monovalent hydrocarbon groups; and $X^-$ is a counter ion, with the proviso that at least one of $-Q^1$, $-Q^2$ and $-Q^3$ is $-CH(R^3)CH(OH)YN^+(R^4)(R^5)(R^6)X^-$.

It should be understood that in this disclosure and the claims that follow that particular "R" and similarly designated groups may exhibit some variation, unless specifically stated otherwise. That is, variation allowed by the overall definition given. For example, if it is stated that $R^{99}$ in a certain chemical structure can be hydrogen, chlorine or a monovalent hydrocarbon, then the $R^{99}$'s in a particular sample of the corresponding material may actually vary among the stated possibilities of hydrogen, chlorine or various monovalent hydrocarbons (and still be covered by a corresponding claim). This variation can be between or within molecules as applicable.

As to optional "incorporated" functional groups, it should be understood that these may be "internal" as well as pendant groups. Such groups would not be included in any tally given for number of carbons, unless otherwise indicated.

It should be understood that in this specification and the claims that follow that "unsupported" silicones and silanes are free silicone and silanes. That is, silicones and silanes that are not covalently bonded to supports such as glass beads. Furthermore, all references to silicones and silanes in this disclosure and the claims that follow should be taken to be to unsupported silicones and silanes, unless indicated otherwise. Examples of supported materials can be found in Talley et al. (U.S. Pat. No. 4,118,316), which is hereby incorporated by reference for same.

For the compositions of the present invention, generally acceptable counter ions include halogen ions, such as chlorine and bromine, as well as others such as acetate and methyl sulfate. Counter ions are preferably non-reactive internally; that is, non-reactive with the corresponding silicone or silane portion of the overall molecule or others like it.

The compositions of the present invention, notably the silicones, have application in personal care including hair, skin and nail conditioning and treatment. They may also be used as antimicrobials, notably the silanes. Some uses of the compositions of the present invention are considered in detail in a companion application to this one, filed the same day and entitled, "Silicon Based Quaternary Ammonium Functional Compositions and Their Applications", which is hereby incorporated by reference.

One preferred embodiment of the compositions of the present invention has the groups $-Q^1$, $-Q^2$ and/or $-Q^3$ (as defined previously or those corresponding) as $-CH_2CH(OH)CH_2N^+(R^4)(R^5)(R^6)X^-$. $R^4$, $R^5$, $R^6$ and $X^-$ are as defined previously especially where $R^4$, $R^5$ and $R^6$ are independently monovalent hydrocarbon groups having up to 20 carbons, preferably methyl, dodecyl or octadecyl.

It should be understood that in the context of this disclosure and the claims that follow that ranges disclosed should be taken to specifically disclose not only the endpoint(s) of the range, but all the values subsumed in the range individually. For example, a stated range of 1 to 10 discloses not only 1 and 10, but also 2, 2.7, 5.5 and all other values in the range. Similarly, a range of C1–C5 hydrocarbons would disclose C2, C3 and C4 hydrocarbons, as well as C1 and C5 hydrocarbons.

Another preferred embodiment of the compositions of the present invention is a silicone comprising the group $-R^1-Z-Q^3$ where such group may be expressed as:

$-R^{17}N(Q^1)R^{18}-N(Q^2)-Q^3$ where, $-R^{17}-$ is a divalent hydrocarbon group, which may optionally incorporate ether or ester functionality, and is covalently bonded to Si in an unsupported silicone;

$-R^{18}-$ is a divalent hydrocarbon group that may optionally incorporate ether or ester functionality;

at least one of $Q^1$, $Q^2$ and $Q^3$ is of the formula $-CH(R^3)CH(OH)YN^+(R^4)(R^5)(R^6)X^-$ with all of $Q^1$, $Q^2$ and $Q^3$ remaining being independently hydrogen or a monovalent hydrocarbon group which may optionally incorporate hydroxy, diol, amide, ether or ester functionality;

Y is a divalent hydrocarbon group;

$R^3$ is a monovalent hydrocarbon group or hydrogen;

$R^4$, $R^5$ and $R^6$ are independently monovalent hydrocarbon groups, especially those having up to 20 carbons, preferably methyl, dodecyl or octadecyl; and $X^-$ is a counter ion.

As to the immediately aforementioned embodiment, as well as to the compositions of the present invention generally (where groups corresponding are present), it is frequently preferred that $R^{17}$ is $CH_2CH(CH_3)CH_2$ or $(CH_2)_3$ and that independently $R^{18}$ is $CH_2CH_2$. Correspondingly and independently, it is often preferred that at least one of $Q^1$, $Q^2$ and $Q^3$ is of the formula $CH_2CH(OH)CH_2N^+(CH_3)_2(R^6)X^-$, where $R^6$ is a monovalent hydrocarbon group, especially one having up to 20 carbons, preferably methyl, dodecyl or octadecyl, and $X^-$ is a counter ion. Where any of $Q^1$, $Q^2$ and $Q^3$ are monovalent hydrocarbon groups, one preference is methyl.

An embodiment of the compositions of the present invention of special interest (referred to herein as "the type I embodiment") is a silicone of average formula (to be taken here and in the claims that follow as based on the silicones molecules and their number present in a given sample):

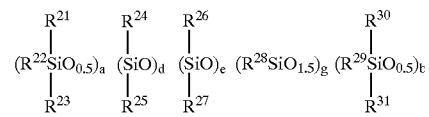

where $R^{21}$, $R^{22}$, $R^{23}$, $R^{30}$ and $R^{31}$ are independently hydroxy or phenoxy, or alkoxy or monovalent hydrocarbon groups (especially, in the latter two instances, those having carbons or less, preferably 1 or 2 carbons);

$R^{24}$, $R^{25}$ and $R^{27}$ are independently monovalent hydrocarbon groups, especially those having 20 carbons or less;

$R^{28}$ is a monovalent hydrocarbon group, especially having 20 carbons or less, or contains nitrogen and may at least in part represent a group or groups of the form —$R^1$—Z—$Q^3$;

$R^{26}$ and $R^{29}$ contain nitrogen and where present represent, at least in part, a group or groups of the form —$R^1$—Z—$Q^3$;

—$R^1$— is either a divalent hydrocarbon group, that may optionally incorporate ether or ester functionality, or —$R^{17}$N($Q^1$)$R^{18}$—, especially —$CH_2CH(CH_3)CH_2$—N($Q^1$)—$CH_2CH_2$— or —$(CH_2)_3$—N($Q^1$)—$CH_2CH_2$— for the latter;

—$R^{17}$— and —$R^{18}$— are independently divalent hydrocarbon groups that may optionally incorporate ether or ester functionality;

—$Q^1$ is —$CH_2CH(OH)CH_2N^+(R^4)(R^5)(R^6)X^-$, hydrogen or a monovalent hydrocarbon group that may optionally incorporate hydroxy, diol, amide, ether or ester functionality;

$R^4$, $R^5$ and $R^6$ are independently monovalent hydrocarbon groups;

$X^-$ is a counter ion;

—Z— is —N($Q^2$)—;

—$Q^3$ and —$Q^2$ are independently —$CH_2CH(OH)CH_2N^+(R^4)(R^5)(R^6)X^-$, hydrogen or a monovalent hydrocarbon group that may optionally incorporate hydroxy, diol, amide, ether or ester functionality;

a, b, d, e and g are greater than or equal to 0;

a=0 to 2+g;

b=0 to 2+g;

d=0 to 500, especially 0 to 400;

e=0 to 100, especially 0 to 50;

g=0 to 100, especially 0 to 5;

a+b is greater than or equal to 2; and e+b>0, with the proviso that at least a portion of $Q^1$, $Q^2$, and $Q^3$ present in the composition, especially where at least 10 percent (preferably 15 to 75 percent and more preferably 20 to 60 percent), with the percentage based on the total number of these groups present in the composition, is —$CH_2CH(OH)CH_2N^+(R^4)(R^5)(R^6)X^-$.

The positions of the R and similarly designated groups shown in the formula in the last mentioned embodiment, as well as all others disclosed or claimed herein, should not be taken as indicating any stereospecificity. Furthermore, it should be understood that the immediately preceding formula is not totally structural; for example, if d was equal to 3 therein, then the composition would have 3 of the subunits corresponding to the d subscript somewhere between each molecule's end groups on average, but not necessarily contiguously.

In the last mentioned embodiment, it is usually preferred that at least 10 percent (more preferably 15 to 75 percent and most preferably 20 to 60 percent) of the total of $Q^1$, $Q^2$ and $Q^3$ (the percentage based on the total number of these groups in the composition) is of the formula $CH_2CH(OH)CH_2N^+(CH_3)_2(R^6)X^-$, where $R^6$ is a monovalent hydrocarbon, especially one having up to 20 carbons, preferably methyl, dodecyl or octadecyl, and $X^-$ is a counter ion. It is often preferred that all remaining $Q^1$, $Q^2$ and $Q^3$ are independently hydrogen or methyl. Additionally, it is usually preferred that (e+b)/(a+b+d+e+g) is greater than or equal to 0.005, more preferably 0.01 to 0.04 and most preferably 0.015 to 0.03.

An embodiment of the compositions of the present invention of great interest (herein "the type II embodiment") is defined as the type I embodiment with the following more specific selections for the groups indicated:

$R^{21}$, $R^{22}$, $R^{23}$, $R^{30}$ and $R^{31}$ are independently hydroxy, or alkoxy or monovalent hydrocarbon groups having 1 to 20 carbons;

$R^{24}$, $R^{25}$ and $R^{27}$ are independently monovalent hydrocarbon groups having 1 to 20 carbons;

$R^{28}$ is a monovalent hydrocarbon group having 1 to 20 carbons, or contains nitrogen and may at least in part represent a group or groups of the form —$R^1$—Z—$Q^3$;

—$R^1$— is either a divalent hydrocarbon group having 1 to 20 carbons, that may optionally incorporate ether or ester functionality, or —$R^{17}$N($Q^1$)$R^{18}$—;

—$R^{17}$— and —$R^{18}$— are independently divalent hydrocarbon groups having 1 to 20 carbons that may optionally incorporate ether or ester functionality;

—$Q^1$ is —$CH_2CH(OH)CH_2N^+(R^4)(R^5)(R^6)X^-$, hydrogen or a monovalent hydrocarbon group having 1 to 20 carbons that may optionally incorporate hydroxy, diol, amide, ether or ester functionality;

$R^4$, $R^5$ and $R^6$ are independently monovalent hydrocarbon groups having 1 to 20 carbons;

$X^-$ is a counter ion;

—$Q^3$ and —$Q^2$ are independently —$CH_2CH(OH)CH_2N^+(R^4)(R^5)(R^6)X^-$, hydrogen or a monovalent hydrocarbon group having 1 to 20 carbons that may optionally incorporate hydroxy, diol, amide, ether or ester functionality;

d=0 to 400;

e=0 to 50;

g=0 to 50; and (e+b)/(a+b+d+e+g)=0.005 to 0.05;

with the proviso that 10 to 75 percent of $Q^1$, $Q^2$, and $Q^3$ present in the composition is —$CH_2CH(OH)CH_2N^+(R^4)(R^5)(R^6)X^-$.

Another embodiment of the compositions of the present invention of great interest (herein "the type III embodiment") is defined as the type I embodiment with the following more specific selections for the groups indicated:

$R^{21}$, $R^{22}$, $R^{23}$, $R^{30}$ and $R^{31}$ are independently hydroxy, methoxy or methyl groups;

$R^{24}$, $R^{25}$ and $R^{27}$ are methyl groups;

$R^{28}$ is a methyl group, or contains nitrogen and may at least in part represent a group or groups of the form —$R^1$—Z—$Q^3$;

—$R^1$— is either a propylene group or —$R^{17}$N($Q^1$)$R^{18}$—;

—$R^{17}$— is a propylene or an isobutylene group and —$R^{18}$— is an ethylene group;

—$Q^1$ is —$CH_2CH(OH)CH_2N^+(R^4)(R^5)(R^6)X^-$, hydrogen or a methyl group;

$R^4$ and $R^5$ are methyl groups;

$R^6$ is a methyl, dodecyl or octadecyl group;

$X^-$ is a counter ion;

—$Q^3$ and —$Q^2$ are independently —$CH_2CH(OH)CH_2N^+(R^4)(R^5)(R^5)X^-$, hydrogen or a methyl group;

d=50 to 150;

e=0 to 10;

g=0 to 5; and (e+b)/(a+b+d+e+g)=0.01 to 0.03, with the proviso that 25 to 40 percent of $Q^1$, $Q^2$, and $Q^3$ present in the composition is —$CH_2CH(OH)CH_2N^+(R^4)(R^5)(R^6)X^-$.

A further embodiment of the compositions of the present invention of special interest is a silane of the formula:

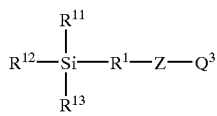

wherein, —$R^{11}$ is a monovalent hydrocarbon group or —$OR^{41}$, where —$R^{41}$ is hydrogen or a monovalent hydrocarbon group;

—$R^{12}$ is a monovalent hydrocarbon group or —$OR^{42}$, where —$R^{42}$ is hydrogen or a monovalent hydrocarbon group;

—$R^{13}$ is a monovalent hydrocarbon group or —$OR^{43}$, where —$R^{43}$ is hydrogen or a monovalent hydrocarbon group;

—$R^1$— is either a divalent hydrocarbon group that may optionally incorporate ether or ester functionality, or —$R^{17}N(Q^1)R^{18}$—;

—$R^{17}$— and —$R^{18}$— are independently divalent hydrocarbon groups that may optionally incorporate ether or ester functionality;

—$Q^1$ is —$CH_2CH(OH)CH_2N^+(R^4)(R^5)(R^6)X^-$, hydrogen or a monovalent hydrocarbon group that may optionally incorporate hydroxy, diol, amide, ether or ester functionality;

$R^4$, $R^5$ and $R^6$ are independently monovalent hydrocarbon groups; and $X^-$ is a counter ion.

—Z— is —$N(Q^2)$—; and

—$Q^3$ and —$Q^2$ are independently —$CH_2CH(OH)CH_2N^+(R^4)(R^5)(R^6)X^-$, hydrogen or a monovalent hydrocarbon group that may optionally incorporate hydroxy, diol, amide, ether or ester functionality, with the proviso that at least one of —$Q^1$, —$Q^2$ and —$Q^3$ is —$CH_2CH(OH)CH_2N^+(R^4)(R^5)(R^6)X^-$.

In the silanes of the present invention, where an R group is a hydrocarbon, it is preferably one having 20 carbons or less, and in the case of $R^4$, $R^5$ and $R^6$, especially and independently methyl, dodecyl or octadecyl. One preferred group of silanes has $R^{11}$, $R^{12}$, and $R^{13}$ as —$OCH_3$ and $R^1$ as —$(CH_2)_3$—.

The methods of the present invention are directed to making silicon based quaternary ammonium functional compositions. In general, these methods comprise reacting:

(1) a quaternary ammonium compound having a substituent group, the substituent group having epoxide or halohydrin functionality, with (2) a silicon based material having an organofunctional group, the silicon based material being an unsupported silicone or silane and the organofunctional group having carboxy or amino functionality.

Reaction takes place between the aforementioned functionalities of the substituent and organofunctional groups.

Reaction may be made to take place by simply putting the reactants in contact, which should be taken as the implied minimum requirement to obtain reaction (performing the "reacting" step) under the circumstances. However, it is usually preferred to mix the reactants and/or heat them, especially to reflux of an added solvent, such as an alcohol like isopropanol. Appropriate catalysts may be employed. It may be advantageous to use an excess of silicone or silane reactant as the presence of residual epoxy or halohydrin reactants in products is usually undesirable (especially the epoxide); such undesirable residual materials would have to be further reacted or removed in an extra step.

It has been found generally that tertiary amines do not add readily to epoxides. This situation can be improved if the reaction mixture is acidified (especially stoichiometrically) or the tertiary amine is pretreated with -acid (converted to its acid salt).

Throughout this disclosure and the claims that follow, it should be understood that "amino" may refer to (at least) primary, secondary and/or tertiary amines. In addition, unless otherwise indicated, reference to an organic acid or base includes one to its ionized form (as well as its salts) and vice versa. For example, reference to a carboxylic acid would include one to the corresponding carboxylate.

One preferred group of epoxy functional quaternary ammonium compounds for use in the application of the methods of the present invention is represented by the formula:

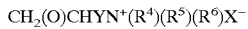

where, Y is a divalent hydrocarbon group, especially methylene;

$R^4$, $R^5$ and $R^6$ are independently monovalent hydrocarbon groups, especially those having up to 20 carbons and preferably methyl, dodecyl or octadecyl; and $X^-$ is a counter ion, especially chloride or bromide.

Specific examples from this group are glycidyl trimethyl ammonium chloride and the corresponding bromide. Non-terminal epoxides may also be used, but terminal epoxides (such as those of the group described here) are generally preferred.

A preferred group of halohydrin functional quaternary ammonium compounds for use in the application of the methods of the present invention is represented by:

where $X^1$ is a halogen, especially chlorine or bromine;

Y is a divalent hydrocarbon group, especially methylene;

$R^4$, $R^5$ and $R^6$ are independently monovalent hydrocarbon groups, especially those having up to 20 carbons and preferably methyl, dodecyl or octadecyl; and $X^-$ is a counter ion, especially chloride or bromide.

Specific examples from this group are 3-chloro-2-hydroxypropyl trimethyl ammonium chloride, 3-chloro-2-hydroxypropyl dimethyldodecyl ammonium chloride, 3-chloro-2-hydroxypropyl dimethyloctadecyl ammonium chloride and the corresponding bromides. (Some combination of these specific halohydrins, other members of the group described here and/or members of the previously recited group of epoxides may also be employed.) Non-terminal halohydrins may also be used, but terminal halohydrins (such as those of the group here) are generally preferred.

Some more specific silicones which are often useful as reactants in the methods of the present invention include those of number average molecular weight 1000 to 100,000 (especially 5000 to 50,000), especially polydimethylsiloxanes that are preferably trimethyl end blocked, and where amino functional, those containing 0.1 to 2.0 milliequivalents amino functionality per gram of silicone (on average based on the amino nitrogen of primary and secondary amino groups in all silicones present in the given sample) being preferred. Examples of amino groups that may be present in these silicones include aminopropyl, aminoethyl aminopropyl or aminoethyl aminoisobutyl.

Often useful as reactants in the methods of the present invention are silanes of the following structure:

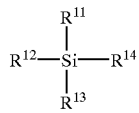

where, $R^{11}$, $R^{12}$ and $R^{13}$ are independently methoxy or ethoxy groups, and $R^{14}$ is an aminopropyl, an aminoethyl aminopropyl or an aminoethyl aminoisobutyl group.

It is of note that the non-silanol silanes of the present invention can be prepared in relatively pure form where synthesis is conducted under anhydrous conditions. Generally, however, it is easier to prepare these silanes in aqueous alcohols. In the latter case, the product will ordinarily be a solution of partially hydrolyzed silanes and silane oligomers; this may be preferred, as silanes used as primers to promote adhesion of organic polymers to mineral surfaces are often applied from aqueous alcohol solutions.

Molecular weight of the products of the methods of the present invention can be controlled by selection of reactants, usually most practically the silicone or silane reactant, as well by selection of the ratio of reactants. Quaternary ammonium content can be controlled through reaction/reactant stoichiometry; that is, by the ratio of reactants. Molecular weight and quaternary ammonium content can be closely correlated to many properties of these materials.

It has been noted that properties of the compositions of the present invention are in large part predictable from their molecular weight in combination with their quaternary ammonium content. The viscosity of these materials (and hence their processing difficulty in most cases) increases fairly regularly with molecular weight, and dramatically at a given molecular weight as the quaternary ammonium content increases. As to water solubility, higher molecular weight materials are generally water insoluble, unless the quaternary ammonium content is very high, but lower molecular weight materials are generally water soluble at much lower (reasonable) quaternary ammonium content.

In one embodiment of the methods of the present invention (specifically of the general class previously recited), the silicone reactant contains on average (taken here and in the claims that follow as based on the total number of silicone reactant molecules used) 0.01 to 8.1, preferably 0.1 to 2.0, more preferably 0.2 to 0.9 and most preferably 0.4 to 0.75 milliequivalents of amine nitrogen per gram, considering only primary and secondary amines. The quaternary ammonium reactant is selected from the group consisting of glycidyl trimethyl ammonium chloride, 3-chloro-2-hydroxypropyl trimethyl ammonium chloride, 3-chloro-2-hydroxypropyl dimethyldodecyl ammonium chloride, 3-chloro-2-hydroxypropyl dimethyloctadecyl ammonium chloride, the corresponding bromide of any of these and some combination of any of these chlorides and bromides. The average molar ratio during reaction of quaternary ammonium reactant to total amine hydrogen in the silicone reactant, considering only primary and secondary amines, is at least 1:10, preferably 1:6 to 9:10. This last ratio, for most practical purposes, has an upper limit of 1:1, since excess quaternary ammonium reactant would have to be removed or further reacted in a later step as its presence in products is usually quite objectionable (especially an epoxide)

The methods of the present invention include those for modifying certain compositions of the present invention to form more complex compositions of the present invention (derivatives). In one particular case, diol or amide functionality is added, the method comprising reacting:

(1) a composition according to the present invention which comprises the group —$R^1$—Z—$Q^3$ as defined previously, wherein at least a portion of $R^1$ is a secondary amine or at least a portion of Z is a primary or secondary amine, with (2) a material, T, where T has organofunctionality selected from the group consisting of lactone, carboxy and epoxy. Specific examples of T include glycidol and gamma butyrolactone.

Reaction may be made to take place by simply putting the reactants in contact, which should be taken as the implied minimum requirement to obtain reaction (perform the "reacting" step) under the circumstances. However, it is usually preferred to mix the reactants and/or heat them, especially to reflux of an added solvent, such as an alcohol like isopropanol. Appropriate catalysts may be employed.

It may be advantageous to use an excess of silicone or silane reactant as the presence of residual halohydrin or epoxide containing reactants in the products is usually undesirable (especially the epoxide) and would have to be removed or further reacted in a later step.

It may be convenient to describe compositions in terms of a method that can be used to make them. This is often termed the "product by process" definition of a composition. The compositions of the present invention should be taken to include products of the methods described herein.

EXAMPLES

The titles given for the examples should be taken as descriptive but not as limiting.

Example 1

Synthesis with an Epoxide at Multiple Stoichiometries/Properties Comparison

Quaternary ammonium functional silicones were prepared from a 150 cS (mm²/s) dimethylsiloxane copolymer containing approximately 2 mole percent aminoethylaminoisobutyl methylsiloxane. This amino functional siloxane thus contained a repeat unit having both primary and secondary amine groups. Theoretically, each aminoethylaminoisobutyl methylsiloxane unit can react with up to three equivalents of glycidyl trimethylammonium chloride.

As a demonstration of the range of materials that can be prepared, samples were made in which 16.7, 33, and 67% of the amine hydrogens were reacted. Although the preferred site of reaction was not determined, the 33% stoichiometry would be sufficient to react one NH in all the primary amines. The procedure for preparing the 33% reacted material follows; that for the other stoichiometries was the same except for proportions of reactants.

54.03 g of the amino functional siloxane just described (0.479 meq amine/g), 2.51 g glycidyl trimethylammonium chloride solution (about 75 weight % in water) and 13.34 g isopropanol were weighed into a three neck 125 ml flask. The reaction mixture was heated to reflux while stirring under static nitrogen, then held at reflux for 4 hours. On cooling, $^{13}C$ Nuclear Magnetic Resonance Spectroscopy ($^{13}C$ NMR) was run and no epoxide was detected, indicating complete reaction of the glycidyl trimethylammonium chloride.

A small sample of the quaternary ammonium silicone product was taken to dryness, by placing a sample in a 50° C. vacuum oven overnight. The dried material was a clear, colorless high viscosity gum. The gum did not dissolve easily in water or alcohol; however, it dissolved readily in tetrahydrofuran (THF), toluene or chloroform.

Gel Permeation Chromatography (GPC) measurements versus polystyrene standards in toluene gave a number average molecular weight of 3870 for the original amino functional siloxane and 3770 for the quaternary ammonium functional siloxane product, thus the dramatic rise in viscosity (see below) is not attributable to a significant increase in molecular weight.

Rheological properties of the dried material were obtained on a Rheometrics SR5000 Stress Controlled Rheometer using 25 mm parallel plate geometry and a 1.00 mm gap. The instrument was set for frequency of 2 rad/sec and an initial stress of 100 dyne/cm$^2$. The instrument was programmed to automatically ramp stress to maintain adequate signal to noise. Rheological properties were acquired during a temperature ramp from 100° C. to 50° C. Quantities measured included G' (the elastic storage modulus), G" (the viscous loss modulus), and η* (the dynamic viscosity).

The viscosities of these materials were very high, with viscosity increasing with increasing concentration of quaternary ammonium groups. A comparison of the theological properties at 70° C. for these materials compared with a high molecular weight silicone gum (a polydimethylsiloxane gum containing some pendant and terminal vinyl functionality having a weight average molecular weight above 500,000 and a viscosity as indicated) appears in Table 1.

TABLE 1

Rheological Properties at 70° C.

| Quaternary Ammonium Functional Siloxane | Initial Amine Content (Mole %) | Targeted % NH Reacted | G' dyne/cm$^2$ | G" dyne/cm$^2$ | η* cP (mPa s) |
|---|---|---|---|---|---|
| A | 2 | 16.7 | 446 | 2,703 | 137,000 |
| B | 2 | 33 | 44,170 | 46,220 | 3,197,000 |
| C | 2 | 67 | 376,400 | 129,000 | 19,900,000 |
| Silicone Gum | — | — | 61,330 | 116,600 | 6,587,000 |

The quaternary functional material in which 67% of the NH groups had been reacted had viscosity and moduli at 70° C. that were substantially higher than a high molecular weight silicone gum. It is of note that the dynamic viscosity has greater temperature dependence for quaternary ammonium functional silicones than for the high molecular weight silicone gum, thus room temperature viscosities for the quaternary ammonium functionals are substantially higher than the 70° C. viscosities reported in Table 1.

Example 2

Synthesis with a Halohydrin 50.83 g of an amino functional siloxane of the type in Example 1 (with 0.474 meq amine/g), 3.84 g of 3-chloro-2-hydroxypropyl trimethyl ammonium chloride (60 weight % in water, Aldrich Chemicals), 57.20 g of isopropanol and 0.96 g of 50 weight % NaOH in water were placed into a 250 ml three neck flask outfitted with a thermometer, mechanical stirrer, and nitrogen inlet. The reaction mixture was heated to reflux and maintained at reflux for 3 hours. The product was suction filtered. A portion of the product was devolatilized in a vacuum oven. The devolatilized material was a clear colorless gum.

Rheological measurements at 70° C., G'=1.88×10$^5$ dynes/cm$^2$, G"=1.71×10$^5$ dynes/cm$^2$, and η*=12,700,000 cP (mPa s). GPC in toluene versus polystyrene standards gave a number average molecular weight of 3370 and a weight average molecular weight of 6660, indicating that the high viscosity was not attributable to an increase in molecular weight (see Example 1).

Example 3

Synthesis with a Halohydrin 50.21 g of an amino functional siloxane of the type in Example 1 (with 0.474 meq amine/g), 10.14 g of 3-chloro-2-hydroxypropyl dimethyldodecyl ammonium chloride (40 weight % in water, Quab® 432 by DeGussa-Huls), and 33.22 g of isopropanol were placed into a 250 ml three neck flask outfitted with a thermometer, mechanical stirrer, and nitrogen inlet. The reaction mixture was heated to reflux and maintained at reflux for 4 hours. A portion of the product was devolatilized in a vacuum oven. The devolatilized material was a clear colorless gum. Rheological measurements at 70° C., G'=12.43 dynes/cm$^2$, G"=1.09×10$^3$ dynes/cm$^2$, and η*=54,500 cP (mPa s).

Example 4

Synthesis with an Amino Terminal Silicone 80.04 g aminopropyl terminated siloxane (DMS-A21 by Gelest, with 0.348 meq amine/g), 5.65 g glycidyl trimethylammonium chloride solution (about 75 weight percent in water), and 21.45 g isopropanol were weighed into a 250 ml flask outfitted with condenser, thermometer and air stirrer. The reaction mixture was brought to and held at reflux for approximately 4.5 hours. A portion of the reaction product was devolatilized in a vacuum oven. The devolatilized material was a clear colorless gum. Rheological measurements at 70° C. showed G'=4.49×10$^4$ dynes/cm$^2$, G"=9.83×10$^4$ dynes/cm$^2$, and η*=5,410,000 cP (mPa s).

Example 5

Synthesis with a Carboxy Functional Silicone

A stirred mixture of 25.9 g of a carboxylic acid terminated polydimethylsiloxane (DMS-B12 by Gelest, number average molecular weight about 1,000) and 30 g of tetrahydrofuran was heated to reflux, at which time 10 g of glycidyl trimethylammonium chloride (approximately 75 weight % in water) was added drop wise. The reaction was held at reflux for approximately 24 hours. A portion of the product was devolatilized in a vacuum oven to give a sticky solid. Product formation was confirmed by $^{13}$C NMR, which showed a significant decrease in epoxide and carboxylic acid as well as the formation of an ester carbonyl group.

Example 6

Synthesis of a Quaternary Ammonium Functional Silane 5.00 g N-(2-aminoethyl)-3-aminopropyl trimethoxysilane, 4.54 g glycidyl trimethylammonium chloride solution (approximately 75 weight percent in water), and 9.49 g of methanol were refluxed for 4 hours under static nitrogen. The product was analyzed by $^{13}$C NMR, which revealed that the epoxide from the glycidyl trimethylammonium chloride had been completely consumed. A drop of the methanol solution placed on a solid substrate dried to a clear film.

The above synthesis actually yields an alcoholic solution of partially hydrolyzed silane and silane oligomers. Preparation of the pure silane could be accomplished by drying a glycidyl trimethylammonium chloride solution in dimethyl-sulfoxide prior to reaction with amine functional silane.

Example 7

Diol Functionality 300.22 grams of an amino functional siloxane of the type in Example 1 (with 0.530 meq amine/g), 15.95 g of glycidyl trimethyl ammonium chloride solution (about 75 weight percent in water), and 66.44 g of isopropanol were weighed into a 3 neck 1000 ml flask outfitted with a condenser, pressure equalizing dropping funnel, air stirrer and temperature probe. The pressure equalizing dropping funnel was charged with 5.82 g glycidol and 14.07 g isopropanol. While under static nitrogen, the flask was heated to reflux. After approximately 2 hours at reflux, the glycidol/isopropanol mixture was added dropwise using the dropping funnel over approximately 10 minutes. Reflux was continued for an additional 2 hours.

A portion of the reaction product was devolatilized in a vacuum oven. The devolatilized material was a clear colorless gum. Rheological measurements at 70° C. showed G'=1.25×10$^5$ dynes/cm$^2$, G"=1.23×10$^5$ dynes/cm$^2$, and η*=8,420,000 cP (mPa s).

Example 8

Amide Functionality 200 grams of an amino functional siloxane of the type in Example 1 (with 0.530 meq amine/g), 10.6 g. of glycidyl trimethyl ammonium chloride solution (approximately 75 weight percent in water), and 54 g of isopropanol were weighed into a 3-neck flask outfitted with a condenser, air stirrer and temperature probe. While under static nitrogen, the flask was heated to reflux. After approximately 2 hours at reflux, 4.6 grams of gamma butyrolactone was added. The reaction mixture was refluxed for an additional 4 hours.

A portion of the reaction product was devolatilized in a vacuum oven. The devolatilized material was a clear colorless gum. Rheological measurements at 70° C. showed G'=4.65×10$^2$ dynes/cm$^2$, G"=4.86×10$^3$ dynes/cm$^2$, and η*=244,000 cP (mPa s).

The preceding specific embodiments should be taken as illustrative and should not be interpreted as limiting the claims, unless otherwise indicated.

That which is claimed is:

1. A silicon based quaternary ammonium functional composition comprising the group:

—R$^1$—Z—Q$^3$ where, —R$^1$— is either a divalent hydrocarbon group, which may optionally incorporate ether or ester functionality, or —R$^{17}$N(Q$^1$)R$^{18}$—, and is covalently bonded to Si in an unsupported silicone or silane;
—Z— is —C(O)O— or—N(Q$^2$)—;
—Q$^3$ is —CH(R$^3$)CH(OH)YN$^+$(R$^4$)(R$^5$)(R$^6$)X$^-$, hydrogen or a monovalent hydrocarbon group that may optionally incorporate hydroxy, diol, amide, ether or ester functionality;
—R$^{17}$— and —R$^{18}$— are independently divalent hydrocarbon groups that may optionally incorporate ether or ester functionality;
—Q$^1$ and —Q$^2$ are independently —CH(R$^3$)CH(OH)YN$^+$(R$^4$)(R$^5$)(R$^6$)X$^-$, hydrogen or a monovalent hydrocarbon group that may optionally incorporate hydroxy, diol, amide, ether or ester functionality;
Y is a divalent hydrocarbon group;
R$^3$ is a monovalent hydrocarbon group or hydrogen;
R$^4$, R$^5$ and R$^6$ are independently monovalent hydrocarbon groups; and
X$^-$ is a counter ion,
with the proviso that at least one of —Q$^1$, —Q$^2$ and —Q$^3$ is —CH(R$^3$)CH(OH)YN$^+$(R$^4$)(R$^5$)(R$^6$)X$^-$.

2. A composition according to claim 1 that is a silicone and wherein,
—R$^1$— is either a divalent hydrocarbon group, or —R$^{17}$N(Q$^1$)R$^{18}$—, and is covalently bonded to Si in an unsupported silicone;
—R$^{17}$— and —R$^{18}$— are independently divalent hydrocarbon groups;
—Q$^1$ is —CH$_2$CH(OH)CH$_2$N$^+$(R$^4$)(R$^5$)(R$^6$)X$^-$, hydrogen or a monovalent hydrocarbon group;
R$^4$, R$^5$ and R$^6$ are independently monovalent hydrocarbon groups
having up to 20 carbons;
X$^-$ is a counter ion;
—Z— is —N(Q$^2$)—;
—Q$^2$ is —CH$_2$CH(OH)CH$_2$N$^+$(R$^4$)(R$^5$)(R$^6$)X$^-$, hydrogen or a monovalent hydrocarbon group; and
—Q$^3$ is —CH$_2$CH(OH)CH$_2$N$^+$(R$^4$)(R$^5$)(R$^6$)X$^-$, hydrogen or a monovalent hydrocarbon group,
with the proviso that at least one of —Q$^1$, —Q$^2$ and —Q$^3$ is —CH$_2$CH(OH)CH$_2$N$^+$(R$^4$)(R$^5$)(R$^6$)X$^-$.

3. A composition according to claim 1 that is a silicone and wherein the group, —R$^1$—Z—Q$^3$, is:

—R$^{17}$N(Q$^1$)R$^{18}$—N(Q$^2$)—Q$^3$ where, —R$^{17}$— is a divalent hydrocarbon group, which may optionally incorporate ether or ester functionality, and is covalently bonded to Si in an unsupported silicone;
—R$^{18}$— is a divalent hydrocarbon group that may optionally incorporate ether or ester functionality;
at least one of Q$^1$, Q$^2$ and Q$^3$ is of the formula
—CH(R$^3$)CH(OH)YN$^+$(R$^4$)(R$^5$)(R$^6$)X$^-$ with all of Q$^1$, Q$^2$ and Q$^3$ remaining being independently hydrogen or a monovalent hydrocarbon group which may optionally incorporate hydroxy, diol, amide, ether or ester functionality
Y is a divalent hydrocarbon group;
R$^3$ is a monovalent hydrocarbon group or hydrogen;
R$^4$, R$^5$ and R$^6$ are independently monovalent hydrocarbon groups; and
X$^-$ is a counter ion.

4. A composition according to claim 3 wherein,
—R$^{17}$— is —CH$_2$CH(CH$_3$)CH$_2$— or —(CH$_2$)$_3$—, and is covalently bonded to Si in an unsupported silicone;
—R$^{18}$— is —CH$_2$CH$_2$—;
at least one of Q$^1$, Q$^2$ and Q$^3$ is of the formula
—CH$_2$CH(OH)CH$_2$N$^+$(CH$_3$)$_2$(R$^6$)X$^-$ with all remaining of Q$^1$, Q$^2$ and Q$^3$ being independently hydrogen or methyl;
R$^6$ is a monovalent hydrocarbon group having up to 20 carbons; and
X$^-$ is a counter ion.

5. A composition according to claim 1 that is a silicone of average formula:

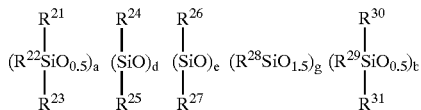

where $R^{21}$, $R^{22}$, $R^{23}$, $R^{30}$ and $R^{31}$ are independently hydroxy, phenoxy, alkoxy or monovalent hydrocarbon groups;

$R^{24}$, $R^{25}$ and $R^{27}$ are independently monovalent hydrocarbon groups;

$R^{28}$ is a monovalent hydrocarbon group, or contains nitrogen and may at least in part represent a group or groups of the form —$R^1$—Z—$Q^3$;

$R^{26}$ and $R^{29}$ contain nitrogen and where present represent, at least in part, a group or groups of the form —$R^1$—Z—$Q^3$;

—$R^1$— is either a divalent hydrocarbon group, that may optionally incorporate ether or ester functionality, or —$R^{17}N(Q^1)R^{18}$—;

—$R^7$— and —$R^{18}$— are independently divalent hydrocarbon groups that may optionally incorporate ether or ester functionality;

—$Q^1$ is —$CH_2CH(OH)CH_2N^+(R^4)(R^5)(R^6)X^-$, hydrogen or a monovalent hydrocarbon group that may optionally incorporate hydroxy, diol, amide, ether or ester functionality;

$R^4$, $R^5$ and $R^6$ are independently monovalent hydrocarbon groups;

$X^-$ is a counter ion;

—Z— is —$N(Q^2)$—;

—$Q^3$ and —$Q^2$ are independently —$CH_2CH(OH)CH_2N^+(R^4)(R^5)(R^6)X^-$, hydrogen or a monovalent hydrocarbon group that may optionally incorporate hydroxy, diol, amide, ether or ester functionality;

a, b, d, e and g are greater than or equal to 0;

a=0 to 2+g;

b=0 to 2+g;

d=0 to 500;

e=0 to 100;

g=0 to 100;

a+b is greater than or equal to 2; and e+b>0, with the proviso that at least a portion of $Q^1$, $Q^2$, and $Q^3$ present in the composition is —$CH_2CH(OH)CH_2N^+(R^4)(R^5)(R^6)X^-$.

6. A composition according to claim 5 wherein, $R^{21}$, $R^{22}$, $R^{23}$, $R^{30}$ and $R^{31}$ are independently hydroxy or phenoxy, or alkoxy or monovalent hydrocarbon groups containing up to 20 carbons;

$R^{24}$, $R^{25}$ and $R^{27}$ are independently monovalent hydrocarbon groups containing up to 20 carbons;

$R^{28}$ is a monovalent hydrocarbon group containing up to 20 carbons;

—$R^1$— is —$CH_2CH(CH_3)CH_2$—$N(Q^1)$—$CH_2CH_2$— or —$(CH_2)_3$—$N(Q^1)$—$CH_2CH_2$—;

at least 10 percent of the total number of $Q^1$, $Q^2$ and $Q^3$ present in the composition is of the formula —$CH_2CH(OH)CH_2N^+(CH_3)_2(R^6)X^-$, with all remaining $Q^1$, $Q^2$ and $Q^3$ independently hydrogen or methyl;

$R^6$ is a monovalent hydrocarbon having up to 20 carbons;

(e+b)/(a+b+d+e+g) is greater than or equal to 0.005;

d=0 to 400;

e=0 to 50; and g=0 to 5.

7. A composition according to claim 5, wherein $R^{21}$, $R^{22}$, $R^{23}$, $R^{30}$ and $R^{31}$ are independently hydroxy, or alkoxy or monovalent hydrocarbon groups having 1 to 20 carbons;

$R^{24}$, $R^{25}$ and $R^{27}$ are independently monovalent hydrocarbon groups having 1 to 20 carbons;

$R^{28}$ is a monovalent hydrocarbon group having 1 to 20 carbons, or contains nitrogen and may at least in part represent a group or groups of the form —$R^1$—Z—$Q^3$;

—$R^1$— is either a divalent hydrocarbon group having 1 to 20 carbons, that may optionally incorporate ether or ester functionality, or —$R^{17}N(Q^1)R^{18}$—;

—$R^{17}$— and —$R^{18}$— are independently divalent hydrocarbon groups having 1 to 20 carbons that may optionally incorporate ether or ester functionality;

—$Q^1$ is —$CH_2CH(OH)CH_2N^+(R^4)(R^5)(R^6)X^-$, hydrogen or a monovalent hydrocarbon group having 1 to 20 carbons that may optionally incorporate hydroxy, diol, amide, ether or ester functionality;

$R^4$, $R^5$ and $R^6$ are independently monovalent hydrocarbon groups having 1 to 20 carbons;

$X^-$ is a counter ion;

—$Q^3$ and —$Q^2$ are independently —$CH_2CH(OH)CH_2N^+(R^4)(R^5)(R^6)X^-$, hydrogen or a monovalent hydrocarbon group having 1 to 20 carbons that may optionally incorporate hydroxy, diol, amide, ether or ester functionality;

d=0 to 400;

e=0 to 50;

g=0 to 50; and (e+b)/(a+b+d+e+g)=0.005 to 0.05;

with the proviso that 10 to 75 percent of $Q^1$, $Q^2$, and $Q^3$ present in the composition is —$CH_2CH(OH)CH_2N^+(R^4)(R^5)(R^6)X^-$.

8. A composition according to claim 5, wherein $R^{21}$, $R^{22}$, $R^{23}$, $R^{30}$ and $R^{31}$ are independently hydroxy, methoxy or methyl groups;

$R^{24}$, $R^{25}$ and $R^{27}$ are methyl groups;

$R^{28}$ is a methyl group, or contains nitrogen and may at least in part represent a group or groups of the form —$R^1$—Z—$Q^3$;

—$R^1$— is either a propylene group or —$R^{17}N(Q^1)R^{18}$—;

—$R^{17}$— is a propylene or an isobutylene group and

—$R^{18}$— is an ethylene group;

—$Q^1$ is —$CH_2CH(OH)CH_2N^+(R^4)(R^5)(R^6)X^-$, hydrogen or a methyl group;

$R^4$ and $R^5$ are methyl groups;

$R^6$ is a methyl, dodecyl or octadecyl group;

$X^-$ is a counter ion;

—$Q^3$ and $Q^2$ are independently —$CH_2CH(OH)CH_2N^+(R^4)(R^5)(R^6)X^-$, hydrogen or a methyl group;

d=50 to 150;

e=0 to 10;

g=0 to 5; and (e+b)/(a+b+d+e+g)=0.01 to 0.03, with the proviso that 25 to 40 percent of $Q^1$, $Q^2$, and $Q^3$ present in the composition is —$CH_2CH(OH)CH_2N^+(R^4)(R^5)(R^6)X^-$.

9. A composition according to claim 1 which is a silane of the formula:

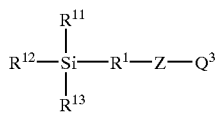

wherein, —$R^{11}$ is a monovalent hydrocarbon group or —$OR^{41}$, where —$R^{41}$ is hydrogen or a monovalent hydrocarbon group;

—$R^{12}$ is a monovalent hydrocarbon group or —$OR^{42}$, where —$R^{42}$ is hydrogen or a monovalent hydrocarbon group;

—$R^{13}$ is a monovalent hydrocarbon group or —$OR^{43}$, where —$R^{43}$ is hydrogen or a monovalent hydrocarbon group;

—$R^1$— is either a divalent hydrocarbon group that may optionally incorporate ether or ester functionality, or —$R^{17}N(Q^1)R^{18}$—;

—$R^{17}$— and —$R^{18}$— are independently divalent hydrocarbon groups that may optionally incorporate ether or ester functionality;

—$Q^1$ is —$CH_2CH(OH)CH_2N^+(R^4)(R^5)(R^6)X^-$, hydrogen or a monovalent hydrocarbon group that may optionally incorporate hydroxy, diol, amide, ether or ester functionality;

$R^4$, $R^5$ and $R^6$ are independently monovalent hydrocarbon groups; and $X^-$ is a counter ion —Z— is —$N(Q^2)$—; and —$Q^3$ and —$Q^2$ are independently —$CH_2CH(OH)CH_2N^+(R^4)(R^5)(R^6)X^-$, hydrogen or a monovalent hydrocarbon group that may optionally incorporate hydroxy, diol, amide, ether or ester functionality, with the proviso that at least one of —$Q^1$, —$Q^2$ and —$Q^3$ is —$CH_2CH(OH)CH_2N^+(R^4)(R^5)(R^6)X^-$.

10. A method of making a silicon based quaternary ammonium functional composition, the method comprising: reacting (1) a quaternary ammonium compound having a substituent group, the substituent group having epoxide or halohydrin functionality, with (2) a silicon based material having an organofunctional group, the silicon based material being an unsupported silicone or silane and the organofunctional group having carboxy or amino functionality.

11. The method of claim 10 wherein the silicon based reactant is a silicone and the organofunctional group is amino functional.

12. The method of claim 10 wherein the silicon based reactant is a silicone and is reacted with an epoxy functional quaternary ammonium compound of formula:

$CH_2(O)CHYN^+(R^4)(R^5)(R^6)X^-$ where, Y is a divalent hydrocarbon group;

$R^4$, $R^5$ and $R^6$ are independently monovalent hydrocarbon groups; and $X^-$ is a counter ion.

13. The method of claim 12 wherein the epoxy functional compound is glycidyl trimethyl ammonium chloride.

14. The method of claim 10 wherein the silicon based reactant is a silicone and is reacted with a halohydrin functional quaternary ammonium compound of formula:

$(X^1)CH_2CH(OH)YN^+(R^4)(R^5)(R^6)X^-$ where $X^1$ is a halogen;

Y is a divalent hydrocarbon group;

$R^4$, $R^5$ and $R^6$ are independently monovalent hydrocarbon groups; and $X^-$ is a counter ion.

15. The method of claim 14 wherein the halohydrin functional compound is 3-chloro-2-hydroxypropyl trimethyl ammonium chloride, 3-chloro-2-hydroxypropyl dimethyldodecyl ammonium chloride, 3-chloro-2-hydroxypropyl dimethyloctadecyl ammonium chloride, or some combination thereof.

16. The method of claim 11 wherein, the silicone reactant contains on average 0.1 to 2.0 milliequivalents of amine nitrogen, considering only primary and secondary amines, per gram of silicone reactant;

the quaternary ammonium reactant is selected from the group consisting of glycidyl trimethyl ammonium chloride, 3-chloro-2-hydroxypropyl trimethyl ammonium chloride, 3-chloro-2-hydroxypropyl dimethyldodecyl ammonium chloride, 3-chloro-2-hydroxypropyl dimethyloctadecyl ammonium chloride, the corresponding bromide of any of these and some combination of any of these chlorides and bromides; and the average molar ratio during reaction of quaternary ammonium reactant to total amine hydrogen in the silicone reactant, considering only primary and secondary amines, is 1:6 to 9:10.

17. The composition produced by the method of claim 10.
18. The composition produced by the method of claim 12.
19. The composition produced by the method of claim 14.
20. The composition produced by the method of claim 16.

21. A method of modifying a silicon based quaternary ammonium functional composition, the method comprising; reacting (1) the composition according to claim 1 wherein at least a portion of $R^1$ is a secondary amine or at least a portion of Z is a primary or secondary amine, with (2) a material T, where T has organofunctionality selected from the group consisting of lactone, carboxy and epoxy.

22. The method of claim 21, wherein T is glycidol or gamma butyrolactone.

* * * * *